(12) United States Patent
Takie et al.

(10) Patent No.: US 12,213,646 B2
(45) Date of Patent: Feb. 4, 2025

(54) ENDOSCOPE HAVING A DISTAL END STRUCTURE FOR HOLDING A COMPOSITE CABLE

(71) Applicant: OLYMPUS CORPORATION, Tokyo (JP)

(72) Inventors: Shuichi Takie, Hachioji (JP); Nau Satake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 17/843,120

(22) Filed: Jun. 17, 2022

(65) Prior Publication Data
US 2022/0322918 A1    Oct. 13, 2022

Related U.S. Application Data (63) Continuation of application No. PCT/JP2020/009229, filed on Mar. 4, 2020.

(51) Int. Cl.
*A61B 1/00* (2006.01)
*A61B 1/05* (2006.01)

(52) U.S. Cl.
CPC ...... *A61B 1/00124* (2013.01); *A61B 1/00114* (2013.01); *A61B 1/051* (2013.01)

(58) Field of Classification Search
CPC ....... H01R 12/51; H01R 12/515; H01R 4/027
See application file for complete search history.

(56) References Cited

U.S. PATENT DOCUMENTS

| | | | | |
|---|---|---|---|---|
| 4,677,471 A | * | 6/1987 | Takamura | A61B 1/05 600/110 |
| 4,706,654 A | * | 11/1987 | Ogiu | A61B 1/05 348/E5.026 |
| 4,745,471 A | * | 5/1988 | Takamura | H04N 23/54 600/109 |

(Continued)

FOREIGN PATENT DOCUMENTS

| | | |
|---|---|---|
| JP | H09-090237 A | 4/1997 |
| JP | H11-295617 A | 10/1999 |

(Continued)

OTHER PUBLICATIONS

International Search Report dated Jun. 2, 2020 received in PCT/JP2020/009229.

*Primary Examiner* — John P Leubecker
(74) *Attorney, Agent, or Firm* — Scully, Scott, Murphy & Presser, P.C.

(57) ABSTRACT

An endoscope includes: a composite cable in which a plurality of cables each including a core wire and an electric insulating coated portion coating the core wire are bundled with an electric insulating outer sheath; a substrate that includes electrodes to which the respective cables are connected; and a cable fixing portion that includes a cable distal end fixing portion holding the plurality of cables in which the core wire and the coated portion are exposed from a distal end surface side of the composite cable, a cable alignment portion aligning the plurality of cables, and a cable body fixing portion holding an end portion of the composite cable on a side where the plurality of cables is exposed, and provided with a through hole having a diameter same as a diameter of an outer periphery of the composite cable.

11 Claims, 11 Drawing Sheets

(56) References Cited

U.S. PATENT DOCUMENTS

| | | | | |
|---|---|---|---|---|
| 4,773,396 | A | * | 9/1988 | Okazaki ............... A61B 1/05 600/109 |
| 4,993,405 | A | * | 2/1991 | Takamura ............. H04N 23/54 600/110 |
| 4,998,182 | A | * | 3/1991 | Krauter ............. A61B 1/00126 439/840 |
| 5,364,292 | A | * | 11/1994 | Bethurum .......... H01R 13/6599 439/607.02 |
| 5,873,816 | A | * | 2/1999 | Kagawa ............. A61B 1/00096 600/110 |
| 5,879,285 | A | | 3/1999 | Ishii |
| 2014/0144697 | A1 | | 5/2014 | Sekido |
| 2014/0220822 | A1 | * | 8/2014 | Keyser ................. H01R 12/53 439/607.46 |
| 2014/0307809 | A1 | * | 10/2014 | Lo ........................... H04B 3/28 375/257 |
| 2017/0108691 | A1 | * | 4/2017 | Kitano ............... A61B 1/00096 |
| 2017/0251914 | A1 | * | 9/2017 | Kitano .................. A61B 1/128 |
| 2018/0064318 | A1 | * | 3/2018 | Kitano .................... A61B 1/01 |
| 2018/0132704 | A1 | * | 5/2018 | Yamada ............ A61B 1/00124 |
| 2018/0249896 | A1 | * | 9/2018 | Mikami ................ A61B 1/044 |
| 2018/0261956 | A1 | * | 9/2018 | Yamaguchi ............ H01R 12/53 |
| 2019/0296537 | A1 | | 9/2019 | Mikami |
| 2019/0393656 | A1 | * | 12/2019 | Wu ........................ H01R 12/70 |
| 2020/0000328 | A1 | * | 1/2020 | Sakai ................ A61B 1/00013 |
| 2020/0084343 | A1 | * | 3/2020 | Sekido ............... A61B 1/00114 |
| 2020/0405136 | A1 | * | 12/2020 | Sakamoto .......... A61B 1/00124 |

FOREIGN PATENT DOCUMENTS

| | | |
|---|---|---|
| JP | 2000-031444 A | 1/2000 |
| JP | 2002-057921 A | 2/2002 |
| JP | 2014-107064 A | 6/2014 |
| JP | 2015-144102 A | 8/2015 |
| WO | 2018/116471 A1 | 6/2018 |

* cited by examiner

ENDOSCOPE HAVING A DISTAL END STRUCTURE FOR HOLDING A COMPOSITE CABLE

CROSS-REFERENCE TO RELATED APPLICATION

This application is a continuation of International Application No. PCT/JP2020/009229, filed on Mar. 4, 2020, the entire contents of which are incorporated herein by reference.

BACKGROUND

1. Technical Field

The present disclosure relates to an endoscope.

2. Related Art

In the related art, an endoscope that is inserted into a subject to perform observation of a region to be examined and the like is known, and is widely used in medical fields and the like. In the endoscope, a composite cable obtained by collecting a plurality of cables is used, and is connected to a substrate in a state where an external coating of the composite cable is removed. The distal end structure of an endoscope is desired to be reduced in diameter and length in consideration of ease of introduction to a patient.

For the purpose of downsizing a distal end structure of an endoscope and simply and easily connecting a cable to a substrate, for example, a technology related to a cable structure in which a plurality of cables having exposed core wires is held by a cable fixing portion in a state where the core wires are exposed is disclosed (see, for example, International Publication No. 2018/116471).

SUMMARY

In some embodiments, an endoscope includes: a composite cable in which a plurality of cables each including a core wire and an electric insulating coated portion coating the core wire are bundled with an electric insulating outer sheath; a substrate that includes electrodes to which the respective cables are connected; and a cable fixing portion that includes a cable distal end fixing portion holding the plurality of cables in which the core wire and the coated portion are exposed from a distal end surface side of the composite cable, a cable alignment portion aligning the plurality of cables, and a cable body fixing portion holding an end portion of the composite cable on a side where the plurality of cables is exposed, and provided with a through hole having a diameter same as a diameter of an outer periphery of the composite cable.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, an endoscope system including a distal end structure will be described as an embodiment for carrying out the disclosure (hereinafter, referred to as "embodiment"). The disclosure is not limited to the following embodiments. Moreover, in the description of the drawings, the same parts are denoted by the same reference numerals. Furthermore, it should be noted that the drawings are schematic, and the relationship between the thickness and width of each member, the ratio of each member, and the like are different from the reality. In addition, parts of the drawings having different dimensions and ratios are included. The same components are denoted by the same reference numerals throughout the description of the embodiments. In addition, the direction in which an image sensor 20 is disposed with respect to a substrate 40 is referred to as "upper", and the direction opposite to the upper direction is referred to as "lower".

First Embodiment

Figure 1:
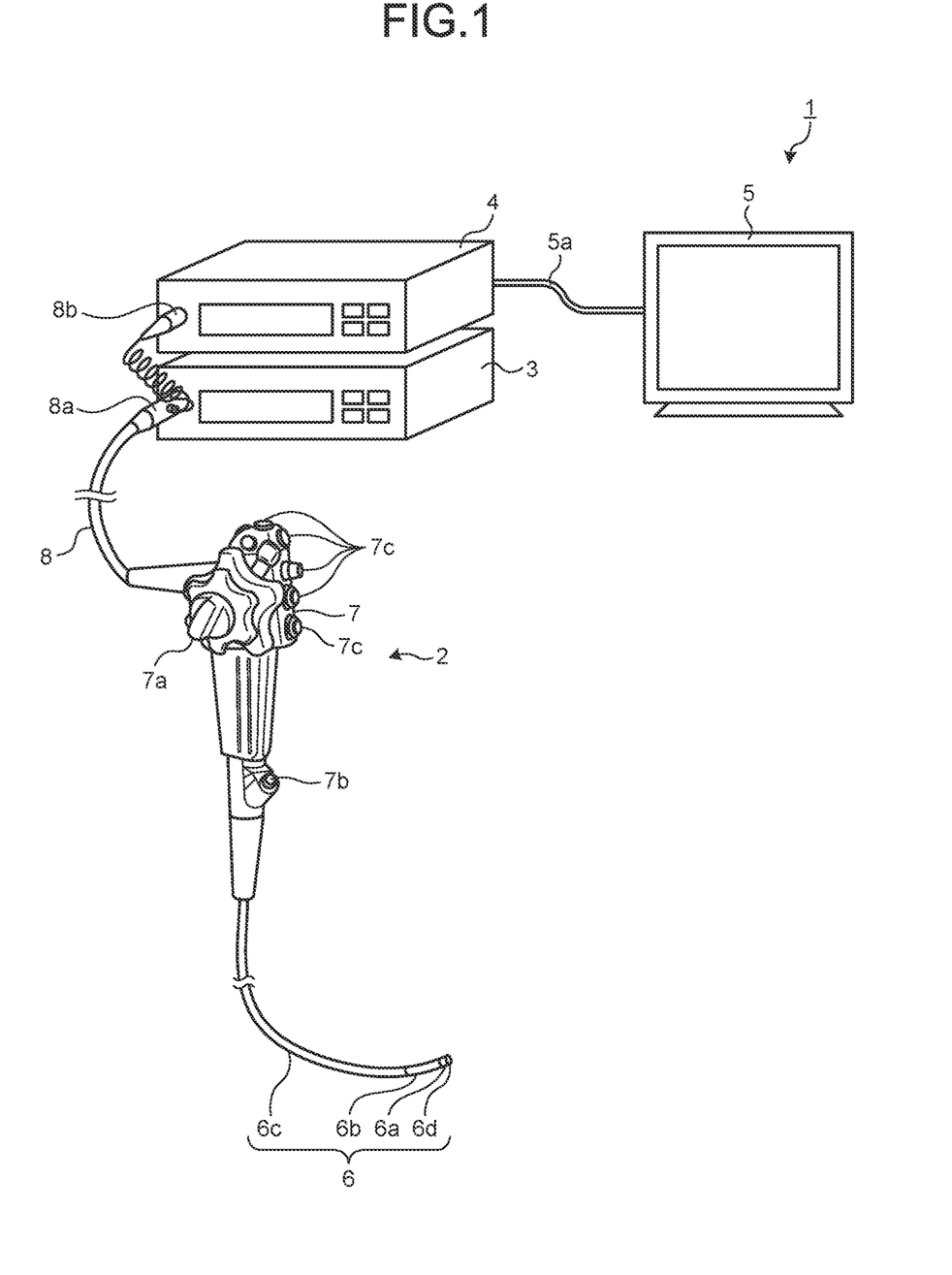
FIG. 1 is a schematic view schematically illustrating an overall configuration of an endoscope system according to a first embodiment of the disclosure.

FIG. 1 is a schematic view schematically illustrating an overall configuration of an endoscope system 1 according to a first embodiment of the disclosure. As illustrated in FIG. 1, the endoscope system 1 according to the first embodiment includes an endoscope 2 that is introduced into a subject and captures an image of the inside of the subject to generate an image signal of the inside of the subject, an information processing apparatus 3 (external processor) that performs predetermined image processing on the image signal captured by the endoscope 2 and controls each unit of the endoscope system 1, a light source apparatus 4 that generates illumination light of the endoscope 2, and a display device 5 that displays an image of the image signal after the image processing by the information processing apparatus 3.

The endoscope 2 includes an insertion portion 6 to be inserted into a subject, an operating unit 7 which is a proximal end portion side of the insertion portion 6 and is gripped by an operator, and a flexible universal cord 8 extending from the operating unit 7.

The insertion portion 6 is realized by using an illumination fiber (light guide cable), an electric cable, an optical fiber, and the like. The insertion portion 6 includes a distal end portion 6a incorporating a distal end structure to be described later, a bendable bending portion 6b including a plurality of bending pieces, and a flexible tube portion 6c having flexibility provided on a proximal end portion side of the bending portion 6b. The distal end portion 6a is provided with an illumination unit that illuminates the inside of the subject via an illumination lens, an observation unit that captures an image of the inside of the subject, an opening portion that communicates with a treatment tool channel, and an air/water supply nozzle (not illustrated).

The operating unit 7 includes a bending knob 7a that bends the bending portion 6b in the vertical direction and the horizontal direction, a treatment tool insertion portion 7b through which a treatment tool such as a biological forceps or a laser scalpel is inserted into the body cavity of the subject, and a plurality of switch units 7c that operate peripheral apparatuses such as the information processing apparatus 3, the light source apparatus 4, an air supply apparatus, a water supply apparatus, and a gas supply apparatus. The treatment tool inserted from the treatment tool insertion portion 7b passes through a treatment tool channel provided inside and comes out from an opening portion 6d at the distal end of the insertion portion 6.

The universal cord 8 is configured using an illumination fiber, a cable, or the like. The universal cord 8 is branched at a proximal end, and one branched end portion is a connector 8a and the other end portion is a connector 8b. The connector 8a is detachable from the connector of the information processing apparatus 3. The connector 8b is detachable from the light source apparatus 4. The universal cord 8 propagates the illumination light emitted from the light source apparatus 4 to the distal end portion 6a via the connector 8b and the illumination fiber. In addition, the universal cord 8 transmits an image signal captured by the image sensor of the distal end structure to be described later to the information processing apparatus 3 via the cable and the connector 8a.

The information processing apparatus 3 performs predetermined image processing on the image signal output from the connector 8a and controls the entire endoscope system 1.

The light source apparatus 4 is configured using a light source that emits light, a condenser lens, and the like. Under the control of the information processing apparatus 3, the light source apparatus 4 emits light from the light source and supplies the light as illumination light for the inside of the subject as a subject to the endoscope 2 connected via the connector 8b and the illumination fiber of the universal cord 8.

The display device 5 is configured using a display or the like using liquid crystal or organic electro luminescence (EL). The display device 5 displays various types of information including an image subjected to predetermined image processing by the information processing apparatus 3 via a video cable 5a. As a result, the operator can observe a desired position in the subject and determine the property by operating the endoscope 2 while viewing the image (in-vivo image) displayed by the display device 5.

Figure 2A:
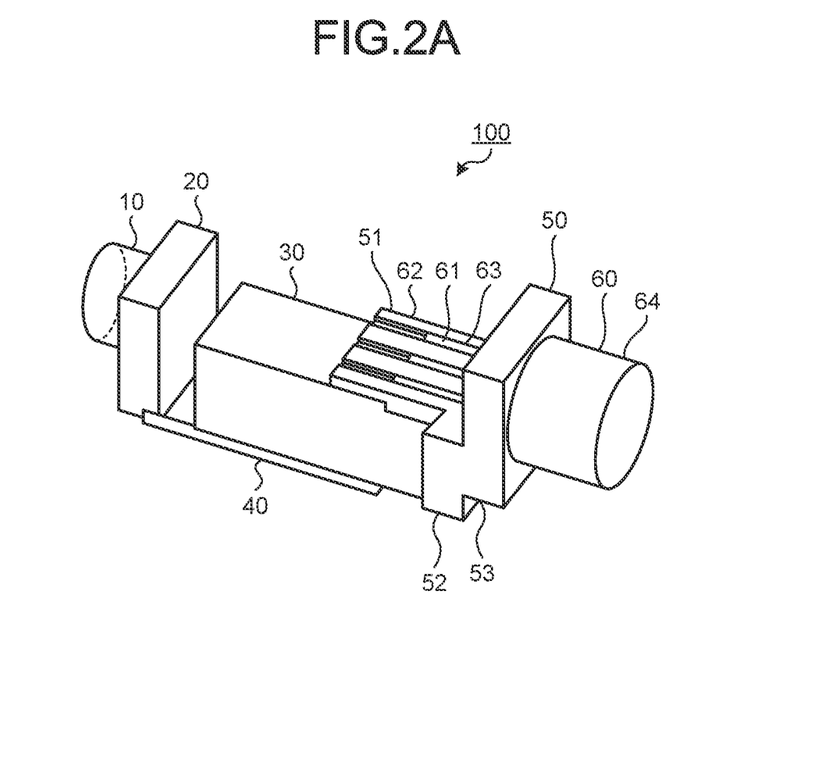
FIG. 2A is a perspective view of a distal end structure used in the endoscope of FIG. 1.
Figure 2B:
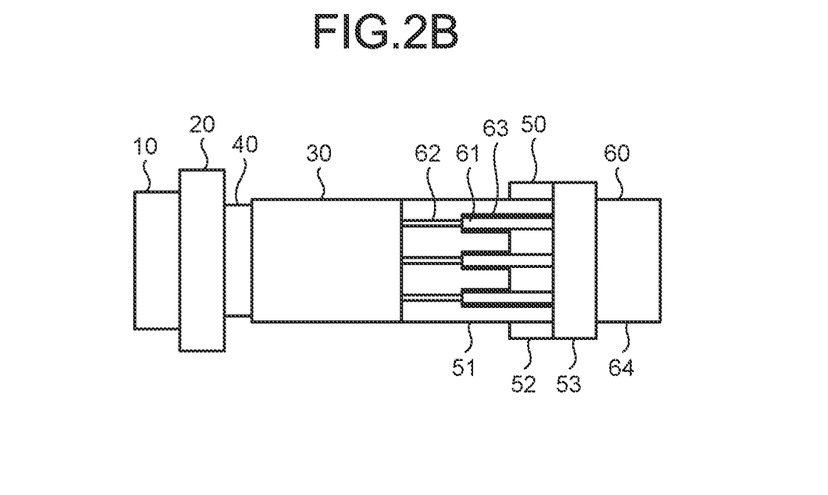
FIG. 2B is a top view of the distal end structure used in the endoscope of FIG. 1.
Figure 2C:
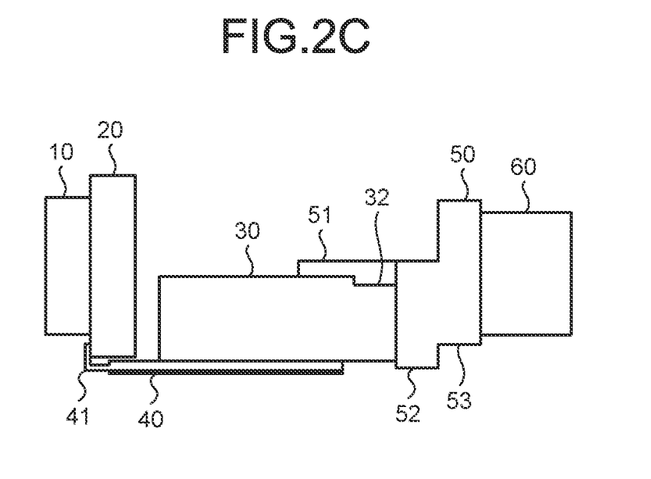
FIG. 2C is a side view of the distal end structure used in the endoscope of FIG. 1.
Figure 3A:
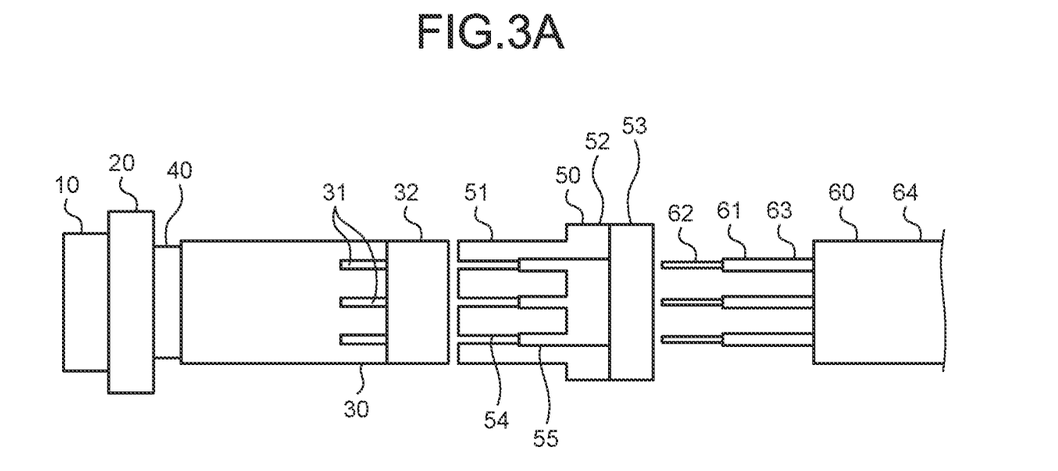
FIG. 3A is an exploded top view of the distal end structure of FIGS. 2A to 2C.
Figure 3B:
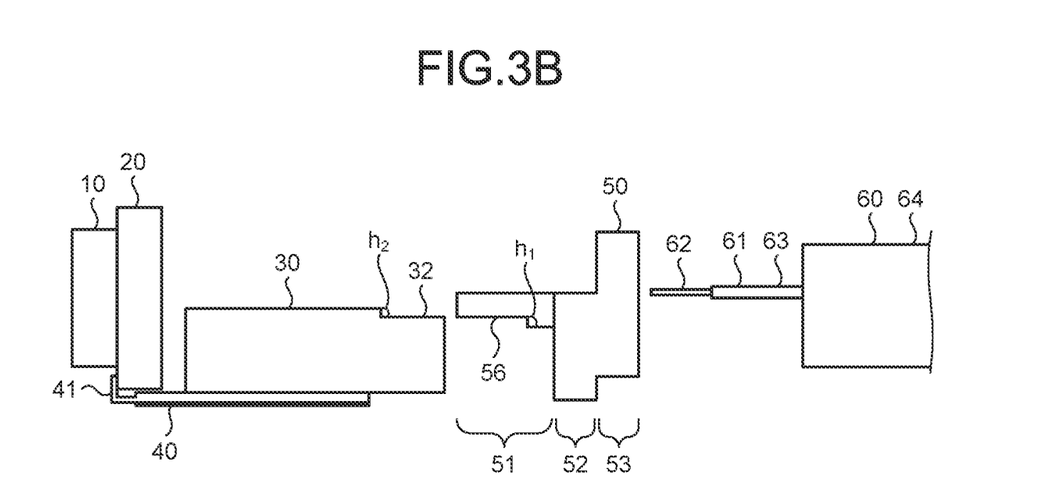
FIG. 3B is an exploded side view of the distal end structure of FIGS. 2A to 2C.
Figure 4A:
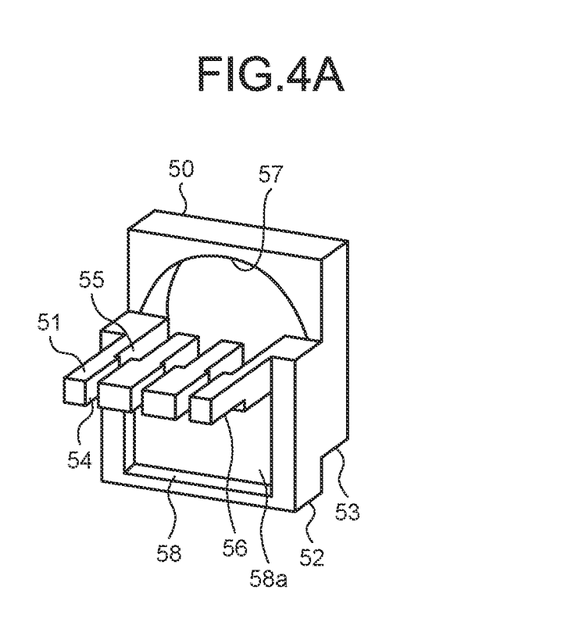
FIG. 4A is a perspective view of a cable fixing portion used in the distal end structure of FIGS. 2A to 2C.
Figure 4B:
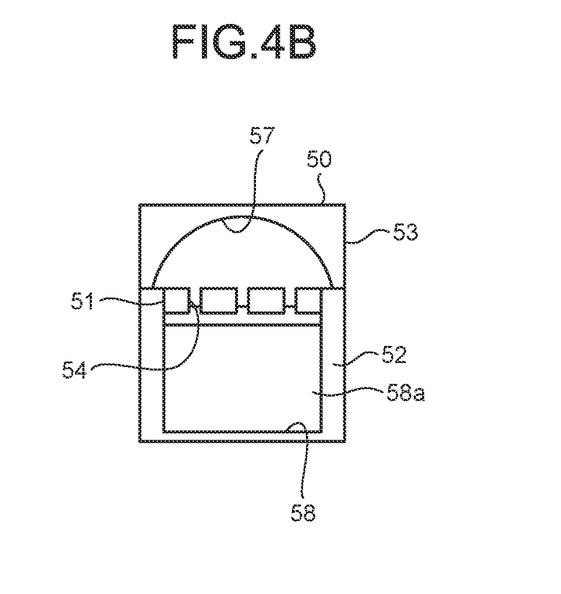
FIG. 4B is a front view of the cable fixing portion used in the distal end structure of FIGS. 2A to 2C.
Figure 4C:
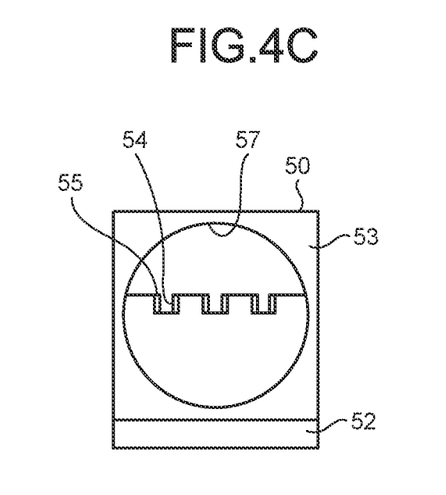
FIG. 4C is a rear view of the cable fixing portion used in the distal end structure of FIGS. 2A to 2C.

Next, a configuration of the distal end structure will be described in detail. FIG. 2A is a perspective view of a distal end structure 100 used in the endoscope 2 of FIG. 1. FIG. 2B is a top view of the distal end structure 100, and FIG. 2C is a side view. FIG. 3A is an exploded top view of the distal end structure 100, and FIG. 3B is an exploded side view. FIG. 4A is a perspective view of a cable fixing portion 50 used in the distal end structure 100, FIG. 4B is a front view of the cable fixing portion 50, and FIG. 4C is a rear view of the cable fixing portion 50.

The distal end structure 100 includes an optical system 10 such as an objective lens, the image sensor 20 that generates an electric signal by receiving light incident by the optical system 10 and performing photoelectric conversion, a first substrate 30, the second substrate 40 that electrically connects the first substrate 30 and the image sensor 20, a composite cable 60, and the cable fixing portion 50 that holds the composite cable 60.

A cover glass for protecting a light receiver is attached to the image sensor 20. An inner lead 41 of the second substrate 40 is connected to an electrode pad (not illustrated) of the image sensor 20. The second substrate 40 is a flexible print circuit (FPC) substrate, and is disposed so as to extend from the image sensor 20 in the optical axis direction.

The first substrate 30 is a multi-layer substrate, electronic components (not illustrated) constituting a drive circuit of the image sensor 20 are mounted or built in, and vias (not illustrated) for electrically conducting a plurality of conductor layers are formed. A connection electrode 31 for connecting a core wire 62 of a cable 61 to be described later is formed at the proximal end of the first substrate 30. In addition, a substrate step portion 32 is formed on the proximal end side from the connection electrode 31 of the first substrate 30 in a direction orthogonal to the optical axis direction.

The composite cable 60 is obtained by bundling a plurality of the cables 61 having the core wire 62 and an electric insulating coated portion 63 coating the core wire 62 with an electric insulating outer sheath 64. The coated portion 63 is cut off at the end portion on the distal end side of the composite cable 60 in order to expose each cable 61. In addition, in the cable 61 exposed from the end portion of the composite cable 60, the coated portion 63 is cut off to expose the core wire 62.

The cable fixing portion 50 includes a cable distal end fixing portion 51 that holds the plurality of cables 61 in which the core wire 62 and the coated portion 63 are exposed from the end surface of the composite cable 60, a cable alignment portion 52 that aligns the plurality of cables 61, and a cable body fixing portion 53 that holds an end portion of the composite cable 60 on a side where the plurality of cables 61 is exposed. FIG. 4A is a perspective view of the cable fixing portion 50, FIG. 4B is a front view, and FIG. 4C is a rear view.

A first opening 54 is formed in the cable distal end fixing portion 51. The core wire 62 of each cable 61 is inserted into the first opening 54, and the core wire 62 is exposed from the upper surface and the lower surface in the inserted state. By providing the first opening 54 at the connection position of the core wire 62, the position of the core wire in the horizontal direction can be defined, and alignment of the first substrate 30 with the connection electrode 31 can be easily performed. The first opening 54 functions as an upper surface opening and a lower surface opening, and since the core wire 62 is exposed from the lower surface opening, connection with the connection electrode of the first substrate 30 can be performed. In addition, since the core wire 62 is exposed from the upper surface opening, the core wire 62 and a conductive member for connection can be directly heated by a heat tool.

A second opening 55 is formed on the proximal end side of the first opening 54 of the cable distal end fixing portion 51. The coated portion 63 of the cable 61 is inserted into the second opening 55. The second opening 55 has a cylindrical shape with an upper surface opened and an inner surface other than the opening portion extending along the coated portion 63.

A step portion 56 is provided on a bottom surface portion of the cable distal end fixing portion 51. A height h1 of the step portion 56 is the same as a height h2 of the substrate step portion 32 of the first substrate 30. The step portion 56 is provided on the lower surface of the first opening 54. The step portion 56 of the cable distal end fixing portion 51 is placed on the connection electrode 31 of the first substrate 30, and a portion provided with the second opening 55, which is the proximal end side of the cable distal end fixing portion 51, is placed on the substrate step portion 32 of the first substrate 30. By placing the cable distal end fixing portion 51 on the upper surface of the first substrate 30, the first substrate 30 and the cable 61 can be aligned in the vertical direction. In addition, by providing the substrate step portion 32 and the step portion 56, it is possible to prevent disconnection or a connection failure due to breakage or the like of the core wire 62 when the core wire 62 is pressed and heated by a heat tool to be connected to the connection electrode 31.

In the cable alignment portion 52, a plurality of the cables 61 bundled in the outer sheath 64 of the composite cable 60 is pulled out from the inside of the outer sheath 64 and aligned. A groove portion 58 for accommodating the proximal end side of the first substrate 30 is formed on the distal end surface side of the cable alignment portion 52. By accommodating the proximal end side of the first substrate 30 in contact with the bottom surface and any two surfaces of the side surfaces in the groove portion 58, it is possible to easily align the first substrate 30 and the cables 61 in the horizontal, vertical, and front-rear directions. In the first embodiment, the groove portion 58 functions as a positioning portion, but the positioning portion only needs to be able to perform alignment in the horizontal direction, and for example, a linear wall portion or an L-shaped wall portion may be provided at one of the left and right end portions on the distal end surface side of the cable alignment portion 52.

The cable body fixing portion 53 has a through hole 57. The diameter of the through hole 57 is substantially the same as the outer periphery of the composite cable 60. By inserting the composite cable 60 into the through hole 57, the end portion of the composite cable 60 on the side where the cables 61 are exposed is held. By holding the outer periphery of the composite cable 60 with the cable body fixing portion 53, even when the extending direction of the composite cable 60 is misaligned with the optical axis direction, misalignment at the boundary between the exposed cables 61 and the end portion of the composite cable 60 can be prevented.

Next, a method of connecting the cables 61 to the first substrate 30 will be described. First, terminal processing is performed in which the outer sheath 64 at the end portion of the composite cable 60 is removed to expose each cable 61 from the composite cable 60, and the coated portion 63 at the exposed end portion of the cable 61 is removed to expose the core wire 62.

The composite cable 60 in which the core wire 62 and the coated portion 63 are exposed stepwise is inserted into the cable fixing portion 50. At this time, the core wire 62 and the coated portion 63 are disposed so as to be positioned in the first opening 54 and the second opening 55 of the cable distal end fixing portion 51.

The cable distal end fixing portion 51 of the cable fixing portion 50 holding the composite cable 60 is placed on the upper surface of the first substrate 30, and the proximal end side of the first substrate 30 is accommodated in contact with a bottom surface 58a and any two surfaces of the side surfaces in the groove portion 58, thereby the first substrate 30 and the cable 61 are aligned in the vertical direction, the horizontal direction, and the front-rear direction. After the alignment of the cable 61, the core wire 62 is connected to the connection electrode 31 by a conductive member such as solder. In the first embodiment, at the time of connection, the connection member is melted by being heated from the upper portion of the cable fixing portion 50 with a heat tool. However, since the heat tool can perform heating while being directly brought into contact with the core wire 62, it is not necessary to perform heating for a long time, and thermal damage to the image sensor 20, the electronic components, and the like can be reduced.

In addition, since the cable 61 to be connected is fixed in a state of being aligned with the first substrate 30 by the cable fixing portion 50, the connection work can be easily performed as compared with the case of individually connecting the core wire 62. Moreover, in the first embodiment, the proximal end side of the first substrate 30 is accommodated and aligned in the groove portion 58 of the cable fixing portion 50, so that the first substrate 30 and the cable 61 can be easily aligned not only in the vertical direction but also in the horizontal direction and the front-rear direction. Furthermore, by providing the substrate step portion 32 and the step portion 56, the core wire 62 can be connected to the connection electrode 31 without being bent, and connection failures can be reduced.

In the first embodiment, the cable fixing portion 50 molded in advance is used, but the disclosure is not limited thereto, and the composite cable 60 subjected to terminal processing may be disposed in a molding frame and insert-molded with a molten resin.

In the cable fixing portion 50 of the first embodiment described above, the core wire 62 is disposed in the first opening 54, but the entire core wire 62 may be exposed without providing the distal end side from the boundary between the first opening 54 and the second opening 55 of the cable distal end fixing portion 51. By adopting a structure in which the entire core wire 62 is exposed without providing the distal end side of the cable distal end fixing portion 51, the heating tool can perform heating while being directly brought into contact with the core wire 62, and thus, the heating time can be further shortened.

Second Embodiment

Figure 5A:
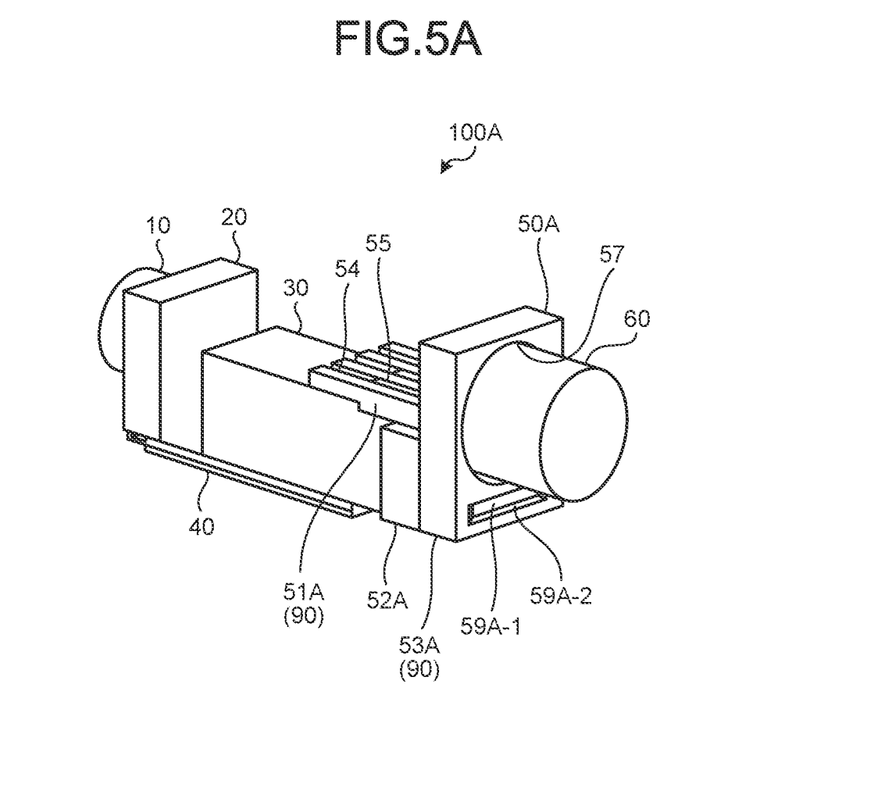
FIG. 5A is a perspective view of a distal end structure according to a second embodiment of the disclosure.
Figure 5B:
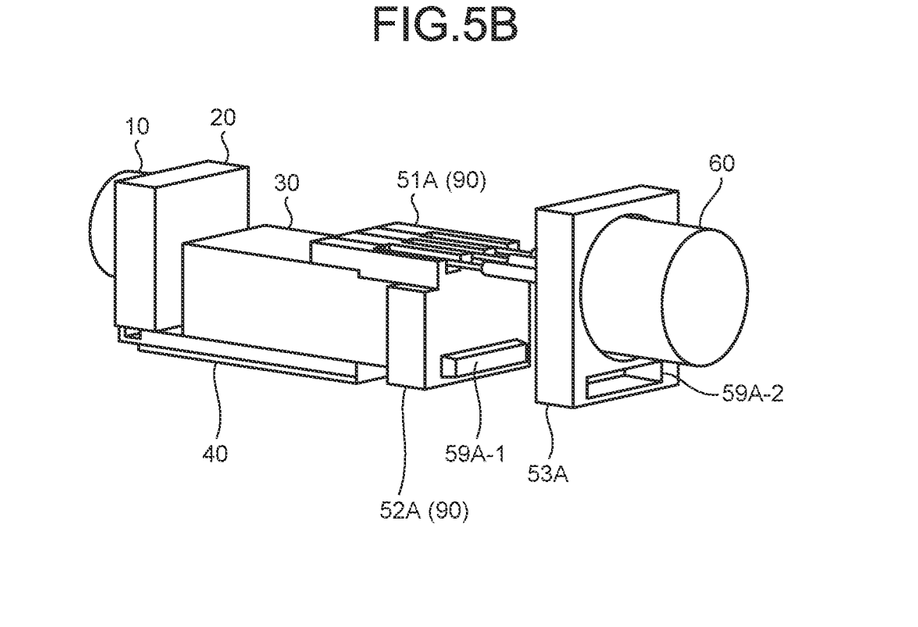
FIG. 5B is an exploded perspective view of the distal end structure of FIG. 5A.

In a second embodiment, the cable fixing portion is divided into two. FIG. 5A is a perspective view of a distal end structure 100A according to the second embodiment of the disclosure. FIG. 5B is an exploded perspective view of the distal end structure 100A.

In the distal end structure 100A, a cable fixing portion 50A is divided into a front end fixing portion 90 including a cable distal end fixing portion 51A and a cable alignment portion 52A, and a cable body fixing portion 53A.

As illustrated in FIGS. 5A and 5B, a first fitting portion 59A-1, which is a rectangular protrusion, is formed on a surface on the proximal end side of the cable alignment portion 52A. In addition, a second fitting portion 59A-2, which is a rectangular through hole, is formed below the through hole 57 of the cable body fixing portion 53A. The cable fixing portion 50A has the same configuration as the cable fixing portion 50 of the first embodiment except that the cable fixing portion 50A is divided and the first fitting portion 59A-1 and the second fitting portion 59A-2 are provided.

In the second embodiment, the composite cable 60 subjected to terminal processing is inserted into the cable body fixing portion 53A. On the other hand, the cable distal end fixing portion 51A of the front end fixing portion 90 is placed on the upper surface of the first substrate 30, and the end portion on the proximal end side of the first substrate 30 is accommodated in the groove portion 58 of the cable alignment portion 52A and is accommodated in contact with the bottom surface and any two surfaces of the side surfaces in the groove portion 58, thereby the first substrate 30 and the front end fixing portion 90 are aligned in the vertical, horizontal, and front-rear directions.

The cable body fixing portion 53A holding the composite cable 60 is brought close to the front end fixing portion 90 aligned with the first substrate 30, and the cable 61 is inserted such that the core wire 62 and the coated portion 63 of the cable 61 are disposed in the first opening 54 and the second opening 55.

The first fitting portion 59A-1 is fitted into the second fitting portion 59A-2 of the cable body fixing portion 53A to align the cable body fixing portion 53A with the front end fixing portion 90. As a result, the first substrate 30 and the cable 61 can be aligned easily and accurately.

The cable fixing portion 50A according to the second embodiment is divided into two parts and thus can easily insert the core wire 62 of the cable 61 into the first opening 54, in addition to exhibiting the same effects as those of the first embodiment. The distal end fixing portion used in the present embodiment is molded in advance, but may be insert-molded on the first substrate 30. By performing insert molding, the alignment can be performed with high accuracy without providing an alignment portion such as the groove portion 58, and the trouble of joining the first substrate 30 and the front end fixing portion can be omitted. The shape of the first fitting portion 59A-1 as a protrusion is not limited to a rectangular shape, and may be a circle, a triangle, or the like.

Third Embodiment

Figure 6A:
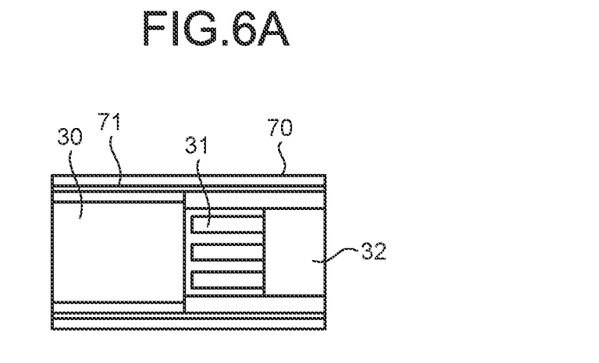
FIGS. 6A to 6C are views for explaining manufacturing of a distal end structure according to a third embodiment of the disclosure.
Figure 6B:
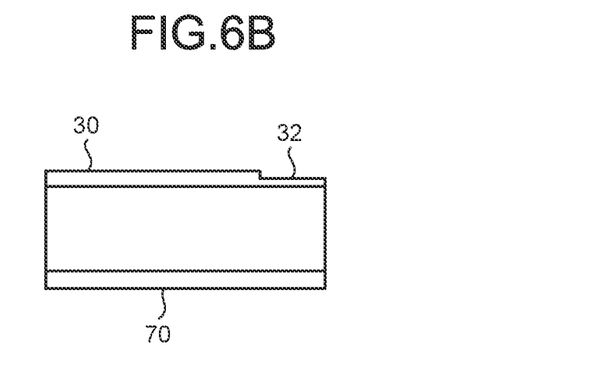
Figure 6C:
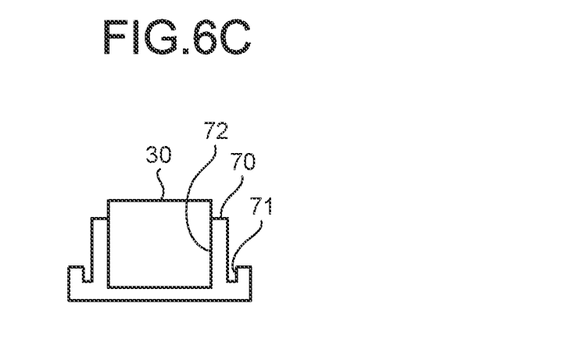

In a third embodiment, the first substrate and the cable are aligned using a stage. FIGS. 6A to 6C are views for explaining manufacturing of the distal end structure according to the third embodiment of the disclosure. FIG. 6A is a top view of the first substrate 30, FIG. 6B is a side view, and FIG. 6C is a front view.

In the third embodiment, when the cable 61 is connected to the first substrate 30, a first substrate fixing portion 70 is used in addition to addition a stage 80. The first substrate fixing portion 70 has a recess 72, and the first substrate 30 is fitted into the recess 72. In addition, the first substrate fixing portion 70 has a fitting portion 71 for alignment with the stage 80 to be described later in a lower portion of each side surfaces.

Figure 7A:
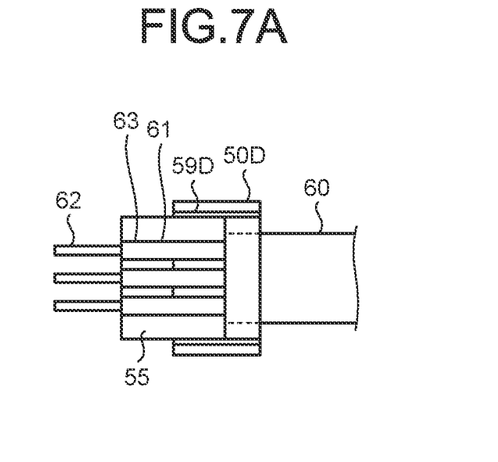
FIGS. 7A to 7C are views for explaining manufacturing of the distal end structure according to the third embodiment of the disclosure.
Figure 7B:
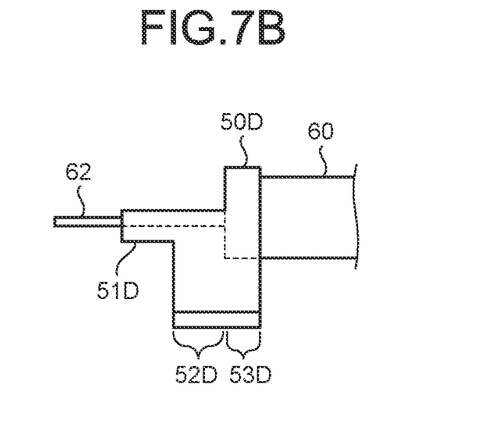
Figure 7C:
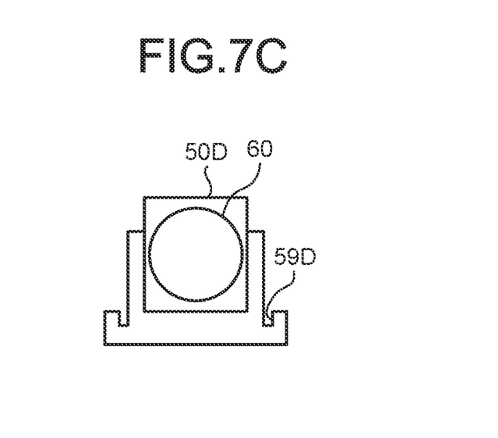

FIGS. 7A to 7C are views for explaining manufacturing of the distal end structure according to the third embodiment of the disclosure. FIG. 7A is a top view of a cable fixing portion 50D that holds the composite cable 60, FIG. 7B is a side view, and FIG. 7C is a front view.

A cable distal end fixing portion 51D of the cable fixing portion 50D does not have a distal end side (a portion provided with the first opening 54 in the first embodiment), and the core wire 62 of the cable 61 protrudes from the distal end side of the cable distal end fixing portion 51D. In addition, a fitting portion 59D for alignment with the stage 80 to be described later is provided in a lower portion of each side surface of a cable alignment portion 52D and a cable body fixing portion 53D. In the cable distal end fixing portion 51D of the cable fixing portion 50D, similarly to the first embodiment, the core wire 62 of the cable 61 may not protrude from the distal end side of the cable distal end fixing portion 51D.

Figure 8A:
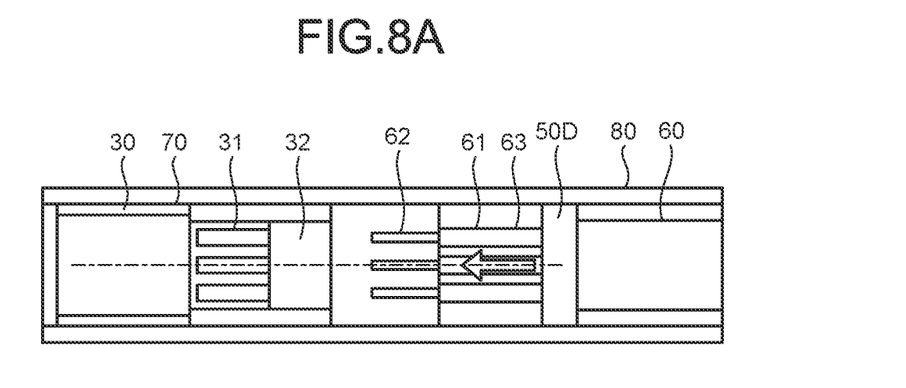
FIGS. 8A to 8C are views for explaining manufacturing of the distal end structure according to the third embodiment of the disclosure.
Figure 8B:
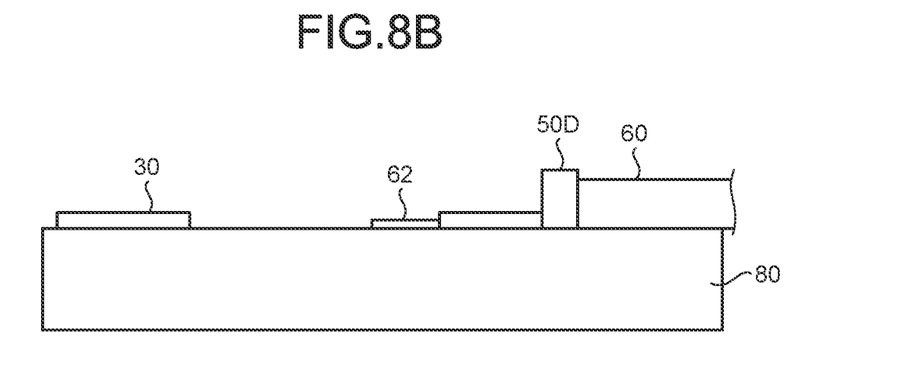
Figure 8C:
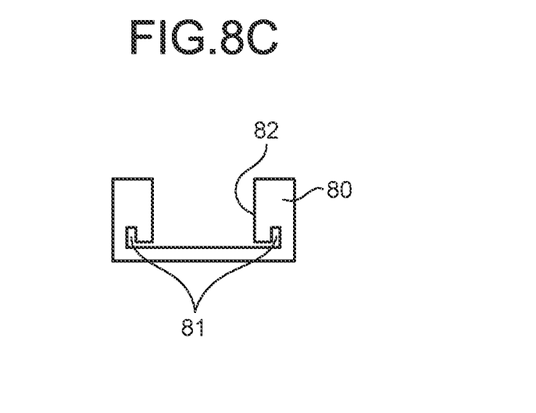

FIGS. 8A to 8C are views for explaining manufacturing of the distal end structure according to the third embodiment of the disclosure. FIG. 8A is a top view of a state in which the first substrate 30 and the cable fixing portion 50D holding the composite cable 60 are disposed in the stage 80, FIG. 8B is a side view, and FIG. 8C is a front view of only the stage 80.

The stage 80 has a recess 82, and the first substrate 30 is fitted into the recess 82 via the first substrate fixing portion 70. The stage 80 has a slide groove 81 in a lower portion of each side surface of the recess 82, and the fitting portion 71 is fitted into the slide groove 81. Similarly, the cable fixing portion 50D is set in the recess 82 by fitting the fitting portion 59D into the slide groove 81.

Figure 9A:
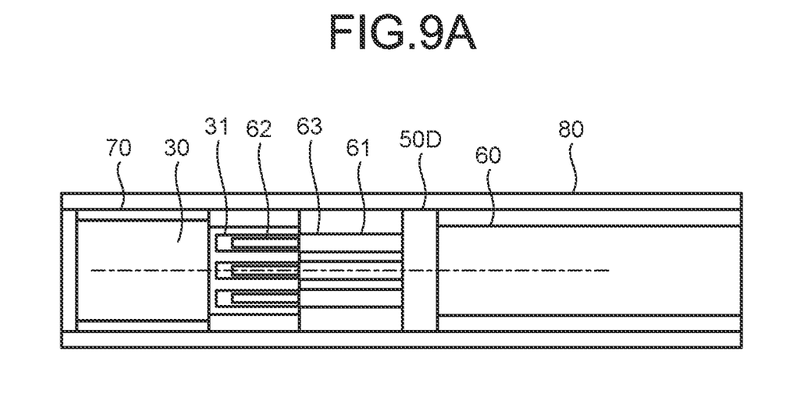
FIGS. 9A and 9B are views for explaining manufacturing of the distal end structure according to the third embodiment of the disclosure.
Figure 9B:
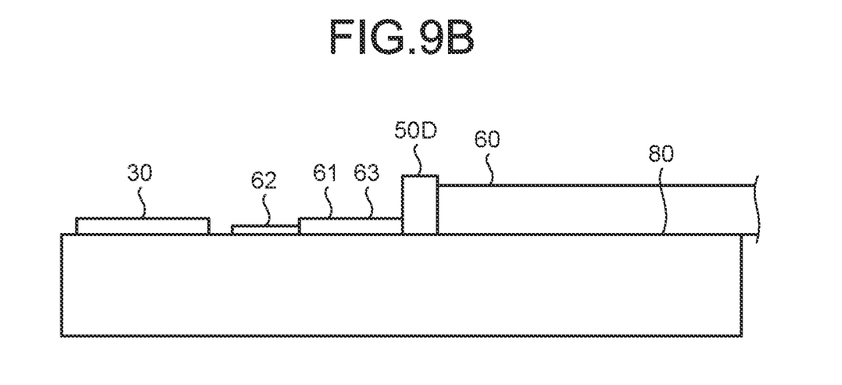

FIGS. 9A and 9B are views illustrating manufacturing of the distal end structure according to the third embodiment of the disclosure. FIG. 9A is a top view of a state in which the cable fixing portion 50D holding the composite cable 60 is placed on the first substrate 30, and FIG. 9B is a side view.

The cable fixing portion 50D holding the composite cable 60 is moved in the direction of the first substrate 30 set in the stage 80, the core wire 62 protruding from the cable distal end fixing portion 51D is disposed on the connection electrode 31, and the bottom surface of the cable alignment portion 52D of the cable fixing portion 50D is placed on the substrate step portion 32 of the first substrate 30. After the placement, the core wire 62 is connected to the connection electrode 31 by a conductive member such as solder. In the third embodiment, at the time of connection, a heating tool can perform heating while being brought into direct contact with the core wire 62, and thus it is not necessary to perform heating for a long time. In addition, by placing the first substrate 30 and the cable fixing portion on the stage 80, it is possible to easily perform alignment in the horizontal direction.

In the distal end structure of the endoscope according to the disclosure, since the end portion of the composite cable on the side of the plurality of exposed cables is also held by the cable fixing portion, it is possible to prevent positional displacement at the boundary portion between the exposed cables and the composite cable, and it is possible to reduce the diameter and improve the reliability of the connection portion.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a composite cable in which a plurality of cables each including a core wire and an electric insulating coated portion coating the core wire are bundled with an electric insulating outer sheath;
   a substrate that includes electrodes to which the respective cables are connected; and
   a cable fixing portion that includes
      a cable distal end fixing portion holding the plurality of cables in which the core wire and the coated portion are exposed from a distal end surface side of the composite cable,
      a cable alignment portion aligning the plurality of cables, and
      a cable body fixing portion holding an end portion of the composite cable on a side where the plurality of cables is exposed, and provided with a through hole having a diameter same as a diameter of an outer periphery of the composite cable;
      wherein the cable distal end fixing portion includes an upper surface opening from which the core wire is exposed and a lower surface opening from which the core wire is exposed, the lower surface opening being formed on a side of a lower surface of the cable distal end fixing portion facing the substrate, the upper surface opening being formed on a side of an upper surface of the cable distal end fixing portion opposite to the lower surface.

2. The endoscope according to claim 1, wherein the cable fixing portion is configured to directly hold an end portion of the composite cable.

3. The endoscope according to claim 1, wherein
   the substrate has a rectangular shape,
   the cable distal end fixing portion holding the plurality of cables is placed on the substrate, and
   a distal end surface side of the cable alignment portion is in contact with a proximal end surface of the substrate.

4. The endoscope according to claim 3, wherein the cable alignment portion includes a positioning portion configured to define a position in a horizontal direction with respect to the substrate on the distal end surface side.

5. The endoscope according to claim 1, wherein the cable fixing portion is divided into a front end fixing portion and the cable body fixing portion, the front end fixing portion including the cable distal end fixing portion and the cable alignment portion.

6. The endoscope according to claim 5, wherein the front end fixing portion is insert-molded on the substrate.

7. An endoscope comprising:
   a composite cable in which a plurality of cables each including a core wire and an electric insulating coated portion coating the core wire are bundled with an electric insulating outer sheath;
   a substrate that includes electrodes to which the respective cables are connected; and
   a cable fixing portion that includes
      a cable distal end fixing portion holding the plurality of cables in which the core wire and the coated portion are exposed from a distal end surface side of the composite cable,
      a cable alignment portion aligning the plurality of cables, and
   a cable body fixing portion holding an end portion of the composite cable on a side where the plurality of cables is exposed, and provided with a through hole having a diameter same as a diameter of an outer periphery of the composite cable;
   wherein the cable fixing portion is divided into a front end fixing portion and the cable body fixing portion, the front end fixing portion including the cable distal end fixing portion and the cable alignment portion;
   the cable alignment portion of the front end fixing portion includes a first fitting portion on a proximal end surface of the cable alignment portion,
   the cable body fixing portion includes a second fitting portion on a distal end surface side of the cable body fixing portion, and
   the front end fixing portion and the cable body fixing portion are positioned by fitting of the first fitting portion and the second fitting portion.

8. The endoscope according to claim 7, wherein the cable fixing portion is configured to directly hold an end portion of the composite cable.

9. The endoscope according to claim 7, wherein
   the substrate has a rectangular shape,
   the cable distal end fixing portion holding the plurality of cables is placed on the substrate, and
   a distal end surface side of the cable alignment portion is in contact with a proximal end surface of the substrate.

10. The endoscope according to claim 9, wherein the cable alignment portion includes a positioning portion configured to define a position in a horizontal direction with respect to the substrate on the distal end surface side.

11. The endoscope according to claim 7, wherein the front end fixing portion is insert-molded on the substrate.

* * * * *